United States Patent [19]
Zunker et al.

[11] Patent Number: 6,090,098
[45] Date of Patent: Jul. 18, 2000

[54] METHOD FOR ALLEVIATING FEMALE URINARY INCONTINENCE

[75] Inventors: Maryann Zunker, Oshkosh; Earle Harry Sherrod, Appleton; Peter Michael Radovanovich, Neenah, all of Wis.

[73] Assignee: Kimberly-Clark Worldwide, Inc., Neenah, Wis.

[21] Appl. No.: 09/217,394

[22] Filed: Dec. 21, 1998

[51] Int. Cl.[7] .................................................. A61M 31/00
[52] U.S. Cl. .................. 604/517; 600/29; 128/DIG. 25; 128/885; 604/279
[58] Field of Search .................................. 128/885, 887, 128/DIG. 25; 600/29–30; 604/517, 279, 544, 329, 330, 500, 515

[56] References Cited

U.S. PATENT DOCUMENTS

| | | | |
|---|---|---|---|
| 1,280,979 | 10/1918 | Ellis . | |
| 2,092,427 | 9/1937 | Ross | 128/285 |
| 2,201,412 | 5/1940 | Stein | 128/285 |
| 2,264,586 | 12/1941 | Ross | 128/285 |
| 2,487,200 | 11/1949 | Trager | 128/285 |
| 2,501,972 | 3/1950 | Seidler | 128/263 |
| 2,711,173 | 6/1955 | Seidler | 128/263 |
| 2,938,519 | 5/1960 | Marco | 128/285 |
| 3,011,495 | 12/1961 | Brecht | 128/285 |
| 3,051,177 | 8/1962 | Wilson | 128/285 |
| 3,079,921 | 3/1963 | Brecht et al. | 128/285 |
| 3,138,159 | 6/1964 | Schmidt | 128/285 |
| 3,369,544 | 2/1968 | Crockford | 128/285 |
| 3,469,286 | 9/1969 | Crockford | 19/144.5 |
| 3,596,328 | 8/1971 | Voss | 19/144.5 |
| 3,643,661 | 2/1972 | Crockford | 128/263 |
| 3,683,915 | 8/1972 | Voss | 128/285 |
| 3,706,311 | 12/1972 | Kokx et al. | 128/285 |
| 3,749,094 | 7/1973 | Duncan | 128/285 |
| 3,762,413 | 10/1973 | Hanke | 128/285 |
| 3,971,378 | 7/1976 | Krantz | 128/285 |
| 4,018,225 | 4/1977 | Elmi | 128/285 |
| 4,019,498 | 4/1977 | Hawtrey et al. | 128/127 |
| 4,212,301 | 7/1980 | Johnson | 128/285 |
| 4,266,546 | 5/1981 | Roland et al. | 128/285 |
| 4,318,407 | 3/1982 | Woon | 128/285 |

(List continued on next page.)

FOREIGN PATENT DOCUMENTS

19602878 C1   9/1997   Germany .

*Primary Examiner*—Corrine McDermott
*Assistant Examiner*—Deborah Blyveis
*Attorney, Agent, or Firm*—Thomas J. Connelly

[57] ABSTRACT

A method for alleviating female urinary incontinence especially during episodes of increased intra-abdominal pressure is disclosed. The method includes the steps of providing a non-absorbent urinary incontinence device having an initial cross-sectional area, an insertion end and a trailing end. The urinary incontinence device also contains a compressed resilient member which is capable of increasing the cross-section area of the urinary incontinence device when expanded. The urinary incontinence device is inserted into a woman's vagina with the insertion end entering first. The vagina is a canal with an inner periphery made up of right and left lateral walls, an anterior wall and a posterior wall. The urinary incontinence device is inserted such that it contacts at least two of the walls. The urinary incontinence device is positioned in the middle third of the length of the vaginal canal with the insertion end aligned adjacent to a woman's urethral sphincter muscle. The urethral sphincter muscle is a part of the urethral tube. The urinary incontinence device cooperates with a woman's symphysis pubis to sandwich the urethral tube therebetween. The resilient member is allowed to expand within the vaginal canal such that at least a portion of the urinary incontinence device increases in cross-sectional area and contacts all four interior walls of the vaginal canal and provides a supportive backdrop for the urethral tube. The urethral tube is then permitted to be compressed upon itself between the urinary incontinence device and the symphysis pubis thereby limiting involuntary urine flow.

21 Claims, 4 Drawing Sheets

U.S. PATENT DOCUMENTS

| | | | |
|---|---|---|---|
| 4,335,721 | 6/1982 | Matthews | 128/285 |
| 4,359,357 | 11/1982 | Friese | 156/201 |
| 4,486,191 | 12/1984 | Jacob | 604/330 |
| 4,668,557 | 5/1987 | Lakes | 428/131 |
| 4,779,928 | 10/1988 | Crowley | 604/329 |
| 4,920,986 | 5/1990 | Biswas | 128/885 |
| 5,041,077 | 8/1991 | Kulick | 600/29 |
| 5,045,079 | 9/1991 | West | 604/329 |
| 5,112,348 | 5/1992 | Glassman | 604/358 |
| 5,158,535 | 10/1992 | Paul et al. | 604/15 |
| 5,273,521 | 12/1993 | Peiler et al. | 604/13 |
| 5,336,208 | 8/1994 | Rosenbluth et al. | 604/329 |
| 5,483,976 | 1/1996 | McLaughlin et al. | 128/885 |
| 5,512,032 | 4/1996 | Kulisz et al. | 600/29 |
| 5,533,990 | 7/1996 | Yeo | 604/363 |
| 5,611,768 | 3/1997 | Tutrone, Jr. | 600/29 |
| 5,618,256 | 4/1997 | Reimer | 600/29 |
| 5,659,934 | 8/1997 | Jessup et al. | 28/120 |
| 5,752,525 | 5/1998 | Simon et al. | 128/885 |
| 5,755,906 | 5/1998 | Achter et al. | 156/217 |
| 5,785,640 | 7/1998 | Kresch et al. | 600/29 |
| 5,795,346 | 8/1998 | Achter et al. | 604/385.1 |
| 5,807,372 | 9/1998 | Balzar | 604/385.1 |
| 5,813,973 | 9/1998 | Gloth | 600/29 |
| 5,873,971 | 2/1999 | Blazar | 156/217 |

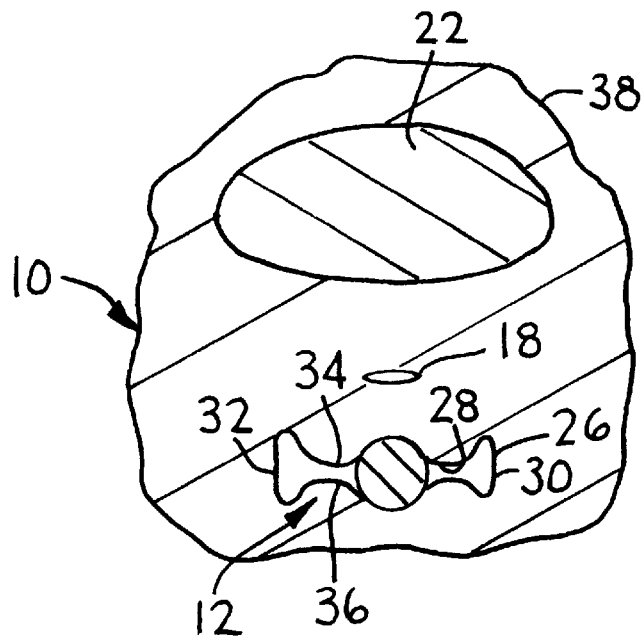
FIG. 2
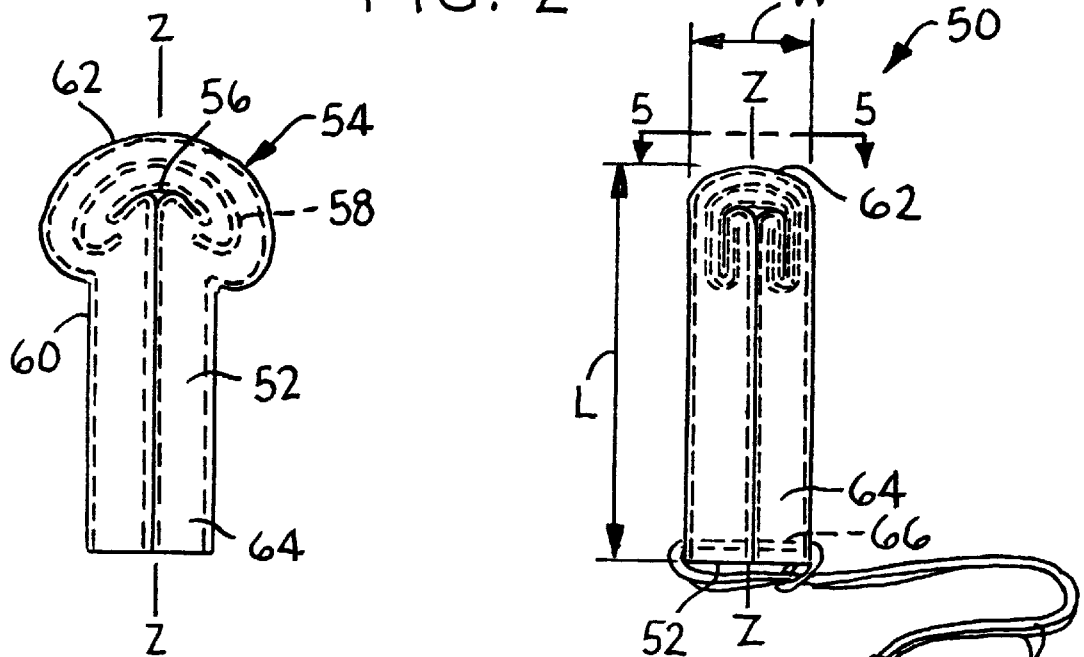
FIG. 3
FIG. 4
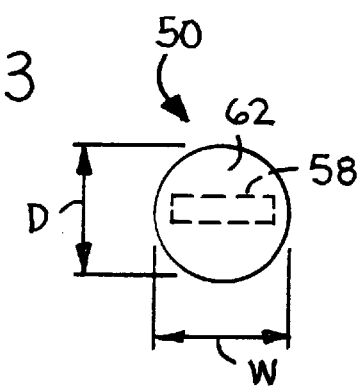
FIG. 5

METHOD FOR ALLEVIATING FEMALE URINARY INCONTINENCE

FIELD OF THE INVENTION

This invention relates to a method for alleviating female urinary incontinence. More specifically, this invention relates to a method for alleviating female urinary incontinence during episodes of increased intra-abdominal pressure.

BACKGROUND OF THE INVENTION

Some women, especially women who have given birth to one or more children, and older women, can experience incidences of involuntary urine loss due to stress urinary incontinence or combined stress and urge incontinence. A sneeze or cough can increase the intra-abdominal pressure impinging on a person's bladder and cause the involuntary release of urine. The frequency and severity of such urine loss can increase as the muscles and tissues near the urethrovaginal myofascial area grow weaker. It has also been recognized that the urinary sphincter muscle, which is located at the upper end of the urethra adjacent to the bladder, works well at sealing off the passing of urine from the bladder to the urethra when it has a round or circular cross-sectional configuration. However, when this passageway becomes distorted into a cross-sectional configuration having more of an elliptical or oval appearance, the sphincter muscle can not close properly, therefore, the tendency for involuntary urine loss increases.

As the world's female population ages, there is an ever increasing need for a non-surgical procedure to reduce the involuntary urine loss commonly associated with "stress urinary incontinence." Today, there are a number of products available for this purpose. Essentially all of these products can only be purchased with a prescription and they need to be physically inserted and/or adjusted by a medical doctor or a nurse practitioner in order to perform correctly. Currently, no products are commercially available, without a prescription, to prevent involuntary urine loss from stress urinary incontinence.

In view of the lack of commercially available, non-prescription urinary incontinence devices, it is recognized that there is a need for a urinary incontinence device which can be purchased without a prescription. There is also a need for a urinary incontinence device which is uncomplicated and therefor more user friendly and can be managed by the consumer without the intervention of a medical practitioner. Furthermore, there is a need for a urinary incontinence device which is easy for woman to insert into and remove from their bodies, be more comfortable to wear and provide psychological and realistic assurance that it is capable of properly performing over an extended period of time.

By having available a method for alleviating female urinary incontinence, especially during episodes of increased intra-abdominal pressure, women will be better able to manage this problem.

SUMMARY OF THE INVENTION

Briefly, this invention relates to a method for alleviating female urinary incontinence especially during episodes of increased intra-abdominal pressure. The method includes the steps of providing a non-absorbent urinary incontinence device having an initial cross-sectional area, an insertion end and a trailing end. The urinary incontinence device also contains a compressed resilient member which is capable of increasing the cross-sectional area of the urinary incontinence device when expanded. The urinary incontinence device is inserted into a woman's vagina with the insertion end entering first. The vagina is a canal with an inner periphery made up of right and left lateral walls, an anterior wall and a posterior wall. The urinary incontinence device is inserted such that it contacts at least two of the walls. The next step is positioning the urinary incontinence device in the middle third of the total length of the vaginal canal with the insertion end aligned adjacent to a woman's urethral sphincter muscle. The urethral sphincter muscle is part of the urethral tube. The urinary incontinence device cooperates with a woman's symphysis pubis to sandwich the urethral tube therebetween. The resilient member is allowed to expand within the vaginal canal such that at least a portion of the urinary incontinence device increases in cross-sectional area and contacts all four interior walls of the vaginal canal and provides a supportive backdrop for the urethral tube. The urethral tube is then permitted to be compressed upon itself between the urinary incontinence device and the symphysis pubis thereby limiting involuntary urine flow.

The general object of this invention is to provide a method for alleviating female urinary incontinence. More specifically, this invention relates to a method for alleviating female urinary incontinence during episodes of increased intra-abdominal pressure.

A more specific object of this invention is to provide a method for alleviating female urinary incontinence during episodes of increased intra-abdominal pressure wherein a non-absorbent device which is placed in a woman's vagina and provides support to a woman's urethra to prevent involuntary urine loss commonly associated with stress urinary incontinence.

Another object of this invention is to provide a method for alleviating female urinary incontinence using a device which is simple to use, easy to insert and remove, and which is comfortable to wear.

A further object of this invention is to provide an efficient and economical method for alleviating female urinary incontinence.

Still another object of this invention is to provide a method for alleviating female urinary incontinence which uses a device which can be purchased by a consumer without a prescription.

Still further, an object of this invention is to provide a method for alleviating female urinary incontinence without disrupting the availability of normal vaginal secretions which are necessary for a healthy vaginal environment.

Other objects and advantages of the present invention will become more apparent to those skilled in the art in view of the following description and the accompanying drawings.

BRIEF DESCRIPTION OF THE DRAWINGS

FIG. 2 is a sectional view taken along line 2—2 of FIG. 1 showing the relaxed cross-sectional configuration of the vaginal canal and the urethra.

FIG. 3 is a side view of one embodiment of a softwind having a dome-shaped portion.

FIG. 4 is a side view of the softwind shown in FIG. 8 after it has been compressed into a urinary incontinence device and a withdrawal string has been attached.

FIG. 5 is top view of the urinary incontinence device shown in FIG. 4 taken along line 5—5.

DETAILED DESCRIPTION OF THE PREFERRED EMBODIMENTS

Figure 1:
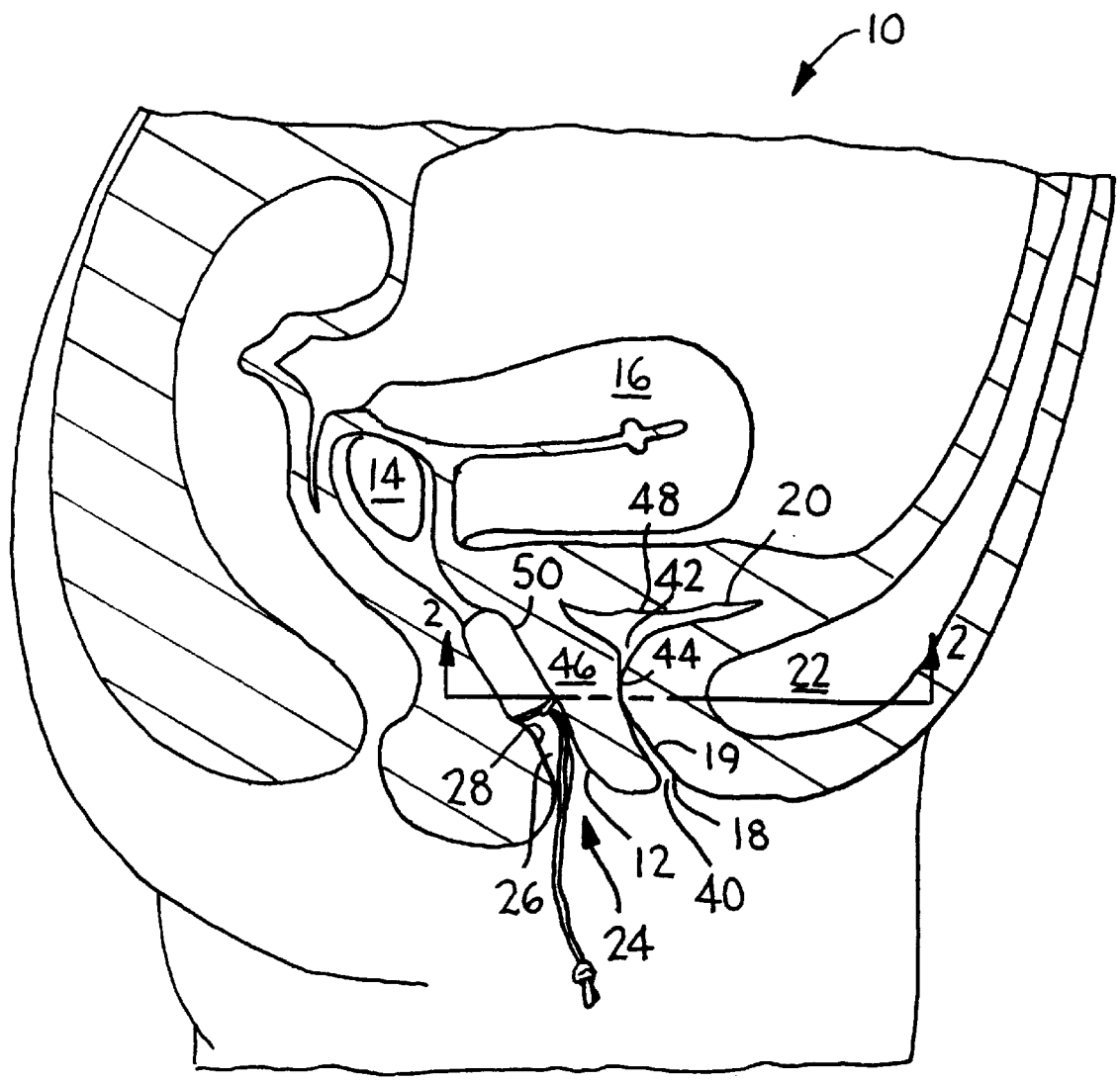
FIG. 1 is a mid-sagittal section of a human torso showing a urinary incontinence device positioned in the vaginal canal and cooperating with the symphysis pubis to allow the urethral tube to be compressed upon itself and alleviate urinary incontinence during episodes of increased intra-abdominal pressure.

Referring to FIGS. 1 and 2, a human torso 10 of a female is depicted showing the vagina 12, a cervix 14, a uterus 16, a urethra 18, a bladder 20 and the symphysis pubis 22. The vagina has an introital opening 24 which exits the human body 10 and contains a vaginal canal 26 which extends from the introital opening 24 to the cervix 14. The vaginal canal 26 has a length which ranges from between about 4 inches to about 6 inches (about 102 millimeters (mm) to about 153 mm) in most woman. The cervix 14 is the entrance to the womb and is located between the upper aspect of the vaginal canal 26 and the uterus 16. The vaginal canal 26 has an inner periphery 28. The inner periphery 28 is made up of right and left lateral walls, 30 and 32 respectively, an anterior wall 34 and a posterior wall 36. The anterior wall 34 is located closest to the urethra 18 and the urethra 18 is located between the symphysis pubis 22 and the vagina 12. The vaginal canal 26 can be divided into three approximately equal sections, each representing a third of the overall length. Each section is approximately 2 inches (approximately 51 millimeters (mm)) in length. The middle third of the vaginal canal 26 is the most important section for alleviating female urinary incontinence because of its proximity to the urethra 18 and is the location where a urinary incontinence device should be positioned. The middle third of the vaginal canal 26 also is horizontally offset from the symphysis pubis 22, which is a bony prominence situated adjacent to a front portion 38 of the human torso 10. Cooperation between a urinary incontinence device positioned in the middle third of the vagina 12 and the symphysis pubis 22 allows the urethra 18 to be compressed upon itself thereby alleviating involuntary urine flow from the bladder 20.

The urethra 18 is a hollow tube 19 which extends from a first opening 40, which exits the human body 10, to a second opening 42 situated at the lower surface of the bladder 20. This urethral tube 19 has a length of about 1.5 inches (about 38 mm) in most women. The urethra 18 functions to discharge urine which is temporarily stored in the bladder 20 from the human body. The urethra 18 has a plurality of urethral sphincter muscles 44 located along the length of the inner periphery of the urethral tube 19. The sphincter muscles 44 are situated below the opening 42 and are ringlike muscles that normally maintains constriction of the urethra 18 to prevent the passage of urine therethrough. The relaxation of the sphincter muscles 44 by normal physiological functioning will permit urine to be voluntarily expelled from the human body.

Referring again to FIG. 1, the human torso 10 further includes musculature and body tissue located in the urethro-vaginal myofascial area 46 which is situated between the vagina 12 and the symphysis pubis 22. The bladder 20 lies posterior to the symphysis pubis 22 and is separated from the rectum by the vagina 12 and the uterus 16. The ureters (not shown), which transport urine from the kidneys (not shown) to the bladder 20, pass from the pelvis to the posterior aspect of the urinary bladder 20. The fundus vesicae 48, into which both ureters run, is adjacent to the anterior wall 34 of the vagina 12.

Referring to FIGS. 3–6, the method for alleviating female urinary incontinence, especially during episodes of increased intra-abdominal pressure, includes providing a non-absorbent urinary incontinence device 50 which can be inserted into a woman's vagina 12. The urinary incontinence device 50 includes a non-absorbent 52 which can be constructed from materials that exhibit little, and preferably, no absorbent characteristics. The non-absorbent, urinary incontinence device 50 differs from a catamenial tampon in that it does not function to absorb body fluid. Instead, the non-absorbent urinary incontinence device 50 is designed to bridge across the vagina 12 and support the musculature and body tissue located in the urethro-vaginal myofascial area 46. By doing so, the urethra 18 can be compressed upon itself sufficiently to intercept the flow of urine and support can be provided to the urinary sphincter muscle 44 so that it can function properly.

For purposes of this invention, a "non-absorbent" is defined as a material which does not absorb significant quantities of moisture by itself. It is to be recognized that virtually all materials will absorb some small quantity of moisture. A fiber is considered to be non-absorbent for present purposes if it will intrinsically gain no more than about 6 percent in weight when a bone dry fiber is maintained at 21°0 C. and at 65 percent relative humidity for 24 hours. Non-absorbent materials include but are not limited to nylons, rayons, spun cellulose, LYCRA®, KEVLAR®, carbon fibers and the like. "LYCRA" and "KELVAR" are trademarks of E. I. DuPont de Nemours & Company which has an office at 1007 Market Street, Wilmington, Del. 19801. One such non-absorbent 52 is a web made from bicomponent fibers which are commercially available from Chisso Corporation having an office at 1411 Broadway, 35th floor, New York, N.Y. Such fibers are sold under the name "Chisso ESC Bicomponent Fiber" and consist of a polypropylene core surrounded by a polyethylene sheath. Fibers that work well have a denier of 3 and are 38 millimeters in length. Other bicomponent fibers made from polypropylene, polyethylene, etc. are commercially available from suppliers such as Exxon and Dow Chemical, as well as from other vendors.

Alternatively, the non-absorbent 52 could be an absorbent material such as a cotton/rayon blend which has been chemically treated with a surfactant to make it non-absorbent. However, materials comprised of truly non-absorbent fibers work best.

Referring to FIG. 3, the urinary incontinence device 50 is shown as a softwind 54 which has been folded upon itself at point 56. The softwind 54 includes the non-absorbent 52 and a resilient member 58. The resilient member 58 can be non-absorbent or at least partially absorbent of body fluids. However, there is no functional advantage to making the resilient member 58 absorbent because the urinary incontinence device 50 does not function in a similar manner as does a catamenial tampon. In fact, the urinary incontinence device 50 functions entirely different from an absorbent catamenial tampon.

The resilient member 58 can be made from a natural or synthetic material which has the ability to quickly recover or return to approximately its original shape and/or dimension.

Such change in the resilient member 58 can be created by changes in the intra-abdominal pressure as a result of laughing, sneezing, coughing, or the like. A resilient material is a material which can return to or resume its original shape or position after being bent, stretched or compressed. The resilient member 58 should also exhibit elasticity and flexibility so that it can be stretched or compressed and still retain the capability of returning to approximately it's original or initial shape.

Two natural materials from which the resilient member 58 can be formed include natural rubber and wool. The number of synthetic materials from which the resilient member 58 can be formed is much greater. Synthetic materials which can be used include: polyolefins, polyurethanes, polyethylene oxide (PEO), polyvinyl alcohol (PVA) as well as blends thereof. The resilient member 58 can also be formed from resilient fibers constructed from polyolefin based fibers, polyethylene oxide fibers, hydrophobic rayon fibers and the like, which preferably will have characteristics similar to those of a resilient foam. Furthermore, the resilient member 58 can be formed from either an open cell or a closed cell foam.

The resilient member 58 can also be made from a wettable foam. An open cell foam which works well and has good resilient properties is commercially available under the trademark ACQUELL®. "ACQUELL" is sold by Sentinel Products Corporation having an office located at 70 Airport Road, Hyannis, Mass. 02601. A polyethylene closed cell foam having good flexibility characteristics also works well. This foam is commercially sold under the trademark VOLARA®. "VOLARA" is available from Voltex, a Division of Sekisui America Corporation having an office located at 100 Shepard Street, Lawrence, Mass. 01843.

The resilient member 58 should also be capable of having what is known as "dry and wet" expansion characteristics. In other words, the resilient member 58 should be made from a material which is capable of expanding or contracting back to or towards its original or initial configuration in a dry state, a wet state or in a semi-dry-wet state. Dry expansion of the urinary incontinence device 50 is beneficial in that the device does not have to be wetted by body fluid before the resilient member 58 is capable of expanding within the vagina.

In FIG. 3, the resilient member 58 is depicted as a narrow strip of material which is rectangular in cross-section. However, the resilient member 58 can have a square, circular, oval or any other desired cross-sectional configuration. Preferably, the resilient member 58 will have a uniform thickness and width. If desired, the dimensions of the resilient member 58 do not have to be uniform. The narrow strip of resilient member 58 can have a length which is less than the length of the non-absorbent 52. The length of the resilient member 58 can be less than about 75 percent (%) of the length of the non-absorbent 52. Preferably the length of the resilient member 58 is less than about 50% of the length of the non-absorbent 52, and most preferably, the length of the resilient member 58 is less than about 40 percent of the length of the non-absorbent 52. However, the length of the resilient member 58 can be equal to the length of the non-absorbent 52, if desired. The resilient member 58 also has a width which can range between about 0.25 inches (about 6.4 mm to about 1.5 inches (about 38.1 mm), preferably between about 0.5 inches (about 12.7 mm) and about 1 inch (about 25.4 mm), and more preferably, about 1 inch (about 25.4 mm). The resilient member 58 also has a thickness which can range between about 0.1 inches (about 2.5 mm) to about 1 inch (about 25.4 mm), preferably less than about 0.5 inches (about 12.7 mm), and most preferably, less than about 0.4 inches (about 10 mm).

When the resilient member 58 has a round or circular cross-sectional configuration, the diameter can range between about 0.25 inches (about 6.4 millimeters) to about 1.5 inches (about 38.1 mm), preferably, from between about 0.25 inches (about 6.4 millimeters) to about 1 inch (about 25.4 mm), and most preferably, less than about 0.5 inches (about 12.7 mm). For odd cross-sectional shapes like an oval, a bilobal, a trilobal, an ellipse, etc. the larger dimension should be no greater than about 2 inches (about 50 mm).

Still referring to FIG. 3, the softwind 54 can contain a liquid permeable or liquid-impermeable cover 60. The cover 60 is an optional element and need not be present to form the urinary incontinence device 50. However, the cover 60 can provide a smooth outer surface which may or may not be chemically treated to facilitate insertion and/or removal into and out of a woman's vagina. When present, the cover 60 should have a length which is equal to or greater than the length of the non-absorbent 52. The cover 60 should have a width which is greater than the width of the non-absorbent 52. The purpose of the greater dimension for the width is that it allows the cover 60 to be folded over upon itself and be bonded to itself by heat, pressure, a combination of heat and pressure, or by some other conventional means known to those skilled in the art. If the cover 60 is formed from a material which does not readily bond to itself, an adhesive, glue or other bonding or fastening medium can be used. If desired, the cover 60 may be simply folded over upon itself.

The cover 60 can be either liquid-permeable or liquid-impermeable. When the cover 60 is liquid-impermeable, it serves to block body fluids from contacting the non-absorbent 52. Since the non-absorbent 52 is not designed to absorb any body fluid, it is not necessary that the cover be liquid-impermeable. Liquid permeable materials include woven and nonwoven materials having a porous substrate. Woven materials include textile fabrics which can be made from rayon, cotton, or polyolefins. The polyolefins can be either staple or continuous filaments. The nonwoven materials can include spunbond, bonded carded webs and hydroentangled webs. Spunbond and bonded carded webs are commercially available from Kimberly-Clark Corporation having an office at 401 N. Lake street, Neenah, Wis. 54956. Another nonwoven material which can be used as the cover 60 is formed from 100 percent polyester fibers held together by a binder. This material is known as powder-bonded-carded web (PBCW). PBCW is commercially available from HDK Industries, Inc. having an office at 304 Arcadia Drive, Greenville, S.C. 29609.

The cover 60 can also be constructed from a liquid-impermeable material. A good liquid-impermeable material is a micro-embossed, polymeric film, such as polyethylene or polypropylene. Bicomponent films can also be used. A preferred liquid-impermeable material is polyethylene film. The thickness of the cover 60 can range from between about 0.1 mm to about 5 mm, preferably less than about 0.5 mm, and most preferably, less than about 0.2 mm.

FIG. 3 represents one embodiment for the softwind 54. It should be noted that the softwind 54 can have two or more folds and can be constructed from two or more layers if desired. The softwind 54, after being folded, should have a length of from between about 1 inch (about 25 mm) to about 3 inches (about 76 mm). A length of from between about 1.5 inches (about 33 mm) to about 2.5 inches (about 63 mm) is preferred. The softwind 54 contains an insertion end 62 and a trailing end 64. The resilient member 58 should be located at least partially in the insertion end 62 so as to allow this end to expand once the urinary incontinence device 50 is positioned within a woman's vagina 12. The purpose of the resilient member 58 is to expand and force the insertion end 62 upward and/or outward so that it can bridge across the cross-sectional area of the user's vagina and contact the walls 30, 32, 34 and 36 of the vaginal canal 26. This action will retain the urinary incontinence device 50 in proper alignment within the vagina 12 and create a force (pressure) which will help support the surrounding tissue located in the urethro-vaginal myofascial area 46. This action will also allow for sufficient pressure transmission across the urethra 18 to interrupt the involuntary flow of urine when intra-abdominal pressure rises. Because of this, the resilient member 58 does not necessarily have to extend throughout the entire length of the softwind 54. The strength of the resilient member 58 will also dictate the size and shape needed to adequately open up the insertion end 62. Depending upon the material from which the resilient member 58 is constructed, it is advantageous to employ a resilient member 58 which has a length which extends across the entire length of the insertion end 62. The resilient member 58 will assure that the softwind 54 will sufficiently open once it is placed within a woman's vagina.

Referring to FIGS. 4 and 5, the softwind 54 is then compressed into the urinary incontinence device 50. The urinary incontinence device 50 can have any desired shape but preferably, it will have a generally cylindrical shape with a circular cross-sectional configuration. An alternative profile would be a rectangular cross-sectional configuration. The urinary incontinence device 50 is depicted as an elongated member having a length L a width W and a depth D, see FIG. 5. When the urinary incontinence device 50 is round in cross-section, its diameter will be equal to the width W and the depth D. The length L of the urinary incontinence device 50 can range from about 0.4 inches (about 10 mm) to about 4.7 inches (about 120 mm), preferably from between about 1.5 inches (about 38 mm) to about 2.5 inches (about 64 mm), and most preferably, the length L is at least about 2 inches (about 51 mm). The width W and the depth D can range from between about 0.2 inches (about 5 mm) to about 2.5 inches (about 64 mm), preferably from between about 0.5 inches (about 12.7 mm) to about 2.3 inches (about 60 mm). Most preferably, the width W and the depth D of the urinary incontinence device 50 is less than about 1.6 inches (about 40 mm).

The insertion end 62 is designed to be the first part of the urinary incontinence device 50 which enters the woman's vagina 12. It should be noted that, while in use, the urinary incontinence device 50 will be entirely positioned within the woman's vagina 12. Since the insertion end 62 contains the fold point 56, it will normally contain a greater amount of non-absorbent material than the trailing end 64. Even though a greater amount of non-absorbent 52 may be present at the insertion end 62, the outside diameter of the insertion end 62 should be equal to the outside diameter of the trailing end 64. The amount of non-absorbent material in the insertion end 62 will have to be densified to a greater extent than the non-absorbent material making up the trailing end 64. By having a greater amount of non-absorbent 52 present at the insertion end 62, the urinary incontinence device 50 is better able to expand and support the musculature and the body tissue located adjacent to the urethra and facilitate urethral compression. This will eliminate the involuntary escape of urine through the urethra 18.

When the urinary incontinence device 50 is formed, the resilient member 58, the non-absorbent 52 and the cover 60, if present, are all compressed. The urinary incontinence device 50 can be compressed radially and lengthwise or it can be compressed only in the radial direction. The resilient member 58 should be located at least in the insertion end 62. The compression step should not detrimentally effect the function of the resilient member 58. In other words, the resilient member 58 has to be capable of expanding outward towards or to its original or initial configuration once the urinary incontinence device 50 is inserted into a woman's vagina 12. The resilient member 58 must be capable of expanding at least a portion of the urinary incontinence device 50 to provide support for a woman's urethra 18 when properly inserted and positioned in a woman's vagina 12.

Still referring to FIG. 4, the compressed urinary incontinence device 50 is pierced near its trailing end 64 to form an aperture or opening 66 which extends partially or completely therethrough. The aperture 66 can be formed perpendicular to the central longitudinal axis X—X or at an angle thereto. Preferably, the aperture 66 is spaced a short distance from the actual end 64. The aperture 66 can be located a distance of from between about 0.1 inches (about 2.5 mm) to about 0.5 inches (about 12.7 mm) from the end 64. Most preferably, the aperture 66 is located about 0.25 inches (about 6.4 mm) from the trailing end 64. The aperture 66 is designed to allow a withdrawal string 68 to be looped therethrough and be secured to the urinary incontinence device 50. The withdrawal string 68 will assist in removing the urinary incontinence device 50 from the vagina 12. The aperture 66 can be formed with a needle, an awl or some other type of piercing device known to those skilled in the art. The withdrawal string 68 is threaded through the aperture 66 and looped upon itself so as to cinch it secure to the urinary incontinence device 50. The free ends of the withdrawal string 68 are then tied in a knot 70 to assure that the withdrawal string 68 will not separate from the urinary incontinence device 50. The knot 70 also serves to prevent fraying of the withdrawal string 68 and to provide a place or point where a woman can grasp the withdrawal string 68 when she is ready to remove the urinary incontinence device 50 from her vagina 12.

It should be noted that the withdrawal string 68 will limit the amount the trailing end 64 can expand while the urinary incontinence device 50 is positioned within the vagina 12. It should also be noted that the withdrawal string 68 can be secured to and/or attached to various areas of the urinary incontinence device 50 and can pass through one or more of the resilient member 58, the non-absorbent 52, the cover 60, if present, or through all three members, if desired. The aperture 66 can alternatively be formed in the softwind 54 before it is compressed and the withdrawal string 68 can be attached either before the softwind 54 is compressed or after the softwind 54 is compressed into the urinary incontinence device 50.

The withdrawal string 68 can be constructed from various types of threads or ribbons. A thread or ribbon made from 100 percent cotton fibers works well. The withdrawal string 68 should have a length which extends beyond the end of the urinary incontinence device 50 of from between about 2 inches (about 51 mm) to about 8 inches (about 203 mm), preferably from between about 4 inches (about 102 mm) to about 6 inches (about 152 mm), and most preferably, about 5 inches (about 127 mm). The withdrawal string 68 can be dyed and/or treated with an anti-wicking agent, such as wax, before being secured to the urinary incontinence device 50. The anti-wicking agent will reduce and hopefully prevent body fluids from wicking along the withdrawal string 68 and contacting the inner surface of a woman's undergarment. A dry, clean withdrawal string 68 is preferred by the user, especially when she goes to remove the urinary incontinence device 50 from her vagina 12.

Figure 6:
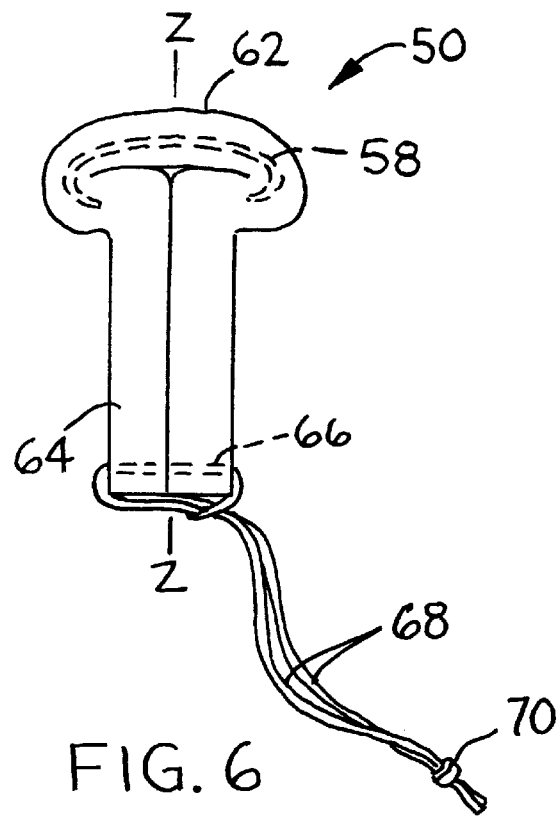
FIG. 6 is a side view of the expanded urinary incontinence device.

Referring now to FIG. 6, the urinary incontinence device 50 is shown with the insertion end 62 expanded as will occur once the device 50 is inserted and positioned within the woman's vagina 12. The resilient member 58 has returned to its initial state and has caused the insertion end 62 to mushroom and expand upward and/or outward so that the urinary incontinence device 50 will come in intimate contact with all four walls 30, 32, 34 and 36 of the vaginal canal 26. In doing so, the urinary incontinence device 50 will occupy the entire cross-sectional void area of the vagina 12 at the position along the length of the vagina 12 where the urinary incontinence device 50 was placed. This will assist the anterior vaginal wall 34 to press against the fundus vesicae 48 of the bladder 20. In addition, the position and proximity of the urinary incontinence device 50 within the vagina 12 will support the urethral sphincter muscle 44 and allow it to function properly. Furthermore, the relative position and proximity of the urinary incontinence device 50 within the vagina 12 will provide a supportive backdrop and cooperate with the symphysis pubis 22 so as to enable the urethra 18 to be compressed upon itself. It should be remembered that while performing the above-identified functions, the urinary incontinence device 50, which is composed of an inert, biocompatible material, will not attract or hold normal bodily secretions and thereby facilitate maintaining a normal vaginal environment.

Referring again to FIG. 1, the urinary incontinence device 50 is shown positioned in the vagina 12 such that it is located in the middle third of the vaginal canal 26 and completely fills the void volume at this location. In other words, the urinary incontinence device 50 occupies approximately the middle 2 inches (about 51 mm) of the vaginal canal 26 and provides a supportive backdrop for the body tissue and muscles located in the urethro-vaginal myofascial area 46. In this position, the urinary incontinence device 50 will be aligned with the upper portion of the urethra 18 and will provide a supportive backdrop for at least half of the urethral tube 19 which has a length of approximately 1.5 inches (approximately 38 mm). During episodes of increased intra-abdominal pressure, the compression that occurs to the urethro-vaginal myofascial area 46 between the symphysis pubis 22 and the urinary incontinence device 50 allows the sphincter muscles 44 to acquire a more normal configuration. The sphincter muscles 44 can then operate properly and the urethral tube 19 is capable of being compressed upon itself. These two functions assist one another in alleviating involuntary urine flow from the bladder 20 through the urethral tube 19 and on to the external opening 40.

Figure 7:
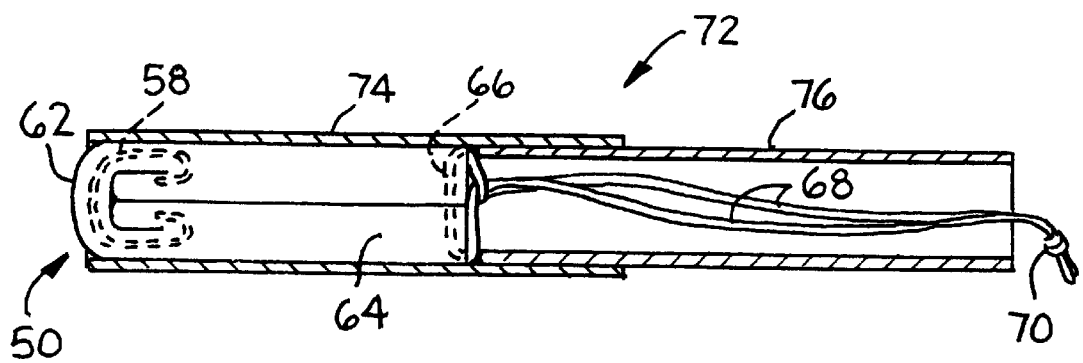
FIG. 7 is a side view of a urinary incontinence device housed in an applicator.

Referring to FIG. 7, the urinary incontinence device 50 is shown being housed in an applicator 72. The applicator 72 will facilitate insertion of the urinary incontinence device 50 into a woman's vagina 12. The applicator 72 can be identical to a tampon applicator, if desired. The applicator 72 is depicted as a two-piece telescoping applicator having a hollow outer tube 74 and a hollow inner tube 76. The urinary incontinence device 50 is positioned within the outer tube 74 such that the inner tube 76, which has a smaller diameter, can be pushed against the trailing end 64. This action will cause the urinary incontinence device 50 to be expelled from the outer tube 74. The applicator 72 can be constructed of paper, cardboard or plastic. One example of an applicator is taught in U.S. Pat. No. 5,795,346 which issued to Achter et al. on Aug. 18, 1998 and is entitled: "TAMPON HAVING A RESILIENT MEMBER." This patent is incorporated by reference and made a part hereof.

It should also be recognized that the urinary incontinence device 50 can be digitally inserted into a woman's vagina 12 if desired. For digital insertion, the woman would use one of her fingers.

Figure 8:
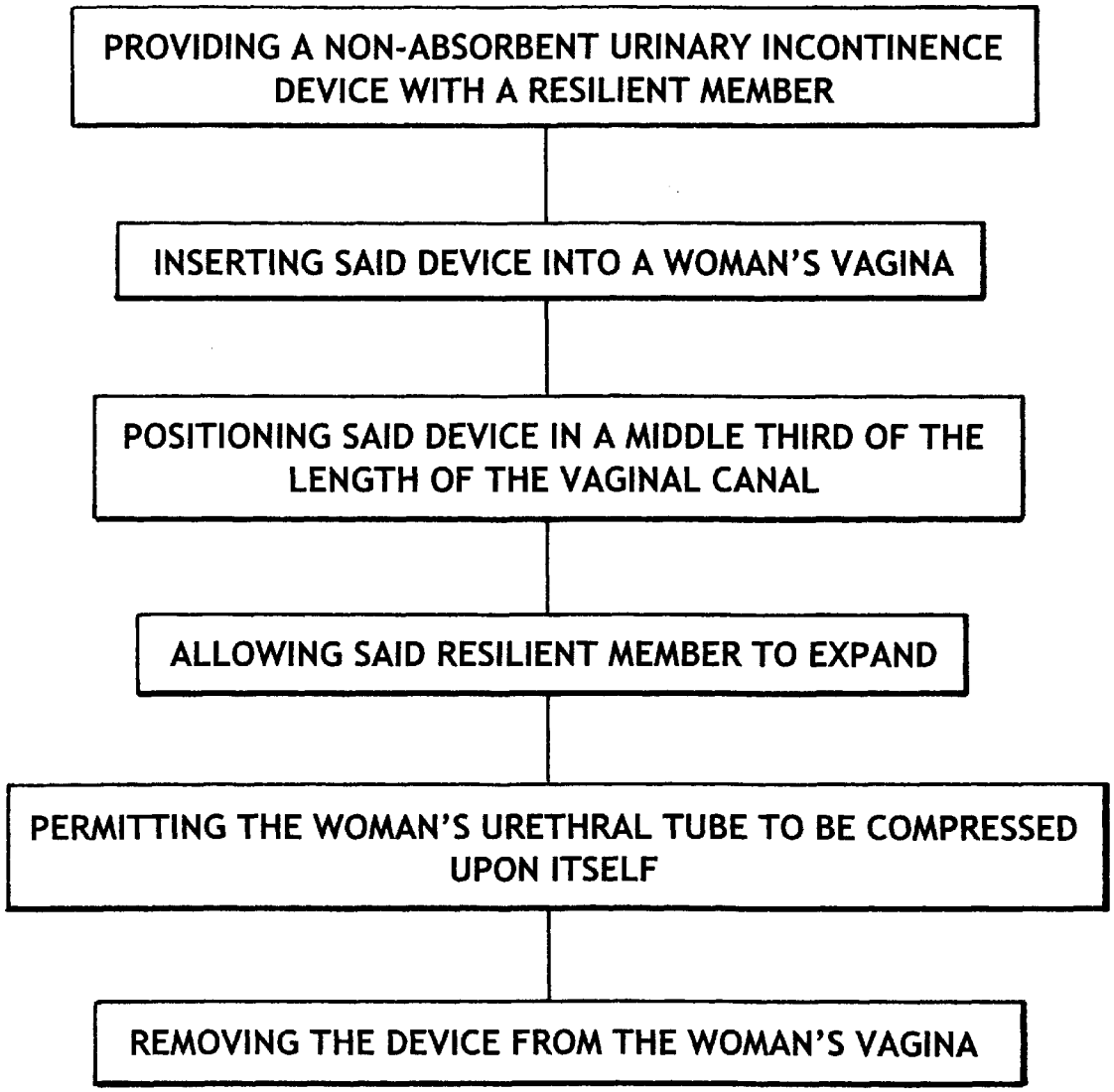
FIG. 8 is a flow diagram of a method for alleviating female urinary incontinence.

Referring to FIG. 8, the method for alleviating female urinary incontinence includes the steps of providing and aligning the non-absorbent urinary incontinence device 50 with the opening 24 of the woman's vagina 12. It should be remembered that the resilient member 58 is in a compressed condition at this time. For the urinary incontinence device 50 to function properly, the resilient member 58 has to be at least partially located approximate to the insertion end 62. The urinary incontinence device 50 is then inserted into the woman's vagina 12 with the insertion end 62 entering first. When inserted, the urinary incontinence device 50 will be in direct contact with at least two of the four wall 30, 32, 34 and 36 which comprise the inner periphery 28 of the vaginal canal 26. Because the vaginal canal 26 is normally maintained in a collapsed state with a plurality of rugosities, it is highly unlikely that the urinary incontinence device 50 will fill the entire void volume. The urinary incontinence device 50 is then positioned in a middle third of the length of the vaginal canal 26 such that the insertion end 62 is aligned adjacent to one of the urethral sphincter muscles 44 which is located in the woman's urethral tube. In this position, the urinary incontinence device 50 cooperates with the symphysis pubis 22 to sandwich the urethral tube therebetween. The method further includes allowing the resilient member 58 to expand within the vaginal canal 26 such that at least a portion of the urinary incontinence device 50 increases in cross-sectional area and contacts all four interior walls 30, 32, 34 and 36 of the vaginal canal 26 and thereby provides a supportive backdrop for the urethral tube 19. Lastly, the urethral tube is permitted to be compressed upon itself between the urinary incontinence device 50 and the symphysis pubis 22 to thereby limit involuntary urine flow. The method can further include the step of removing the urinary incontinence device 50 from the woman's vagina 12.

As mentioned above, the urinary incontinence device 50 can be housed in an applicator 72 prior to use. The applicator 72 will assist in providing a comfortable insertion as well as retaining the urinary incontinence device 50 in a compressed state until it is ready for use. Once the urinary incontinence device 50 is removed from the applicator 72 and inserted into a woman's vagina 12, the resilient member 58 will be able to expand to a non-compressed state. The resilient member 58 should be capable of expanding up to about 25% from its compressed state, preferably up to about 50% from its compressed state, and most preferably, up to about 100% from its compressed state.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. A method for alleviating female urinary incontinence comprising the steps of:

a) providing a non-absorbent urinary incontinence device having an initial cross-sectional area and an insertion end and a trailing end, said urinary incontinence device containing a non-absorbent material made of fibers and a compressed resilient member which is capable of increasing said cross-sectional area of said urinary incontinence device when expanded;

b) inserting said urinary incontinence device into a woman's vagina with said insertion end entering first, said vagina having a vaginal canal with an inner periphery made up of right and left lateral walls, an anterior wall and a posterior wall, and said urinary incontinence device contacting at least two of said walls;

c) positioning said urinary incontinence device in a middle third of the length of said vaginal canal with said insertion end aligned adjacent to a woman's urethral sphincter muscle which is a part of a woman's urethral tube, and said urinary incontinence device cooperating with a woman's symphysis pubis to sandwich said urethral tube therebetween;

d) allowing said resilient member to expand within said vaginal canal such that at least a portion of said urinary incontinence device increases in cross-sectional area and contacts all four interior walls of said vaginal canal and provides a supportive backdrop for said urethral tube; and e) permitting said urethral tube to be compressed upon itself between said urinary incontinence device and said symphysis pubis thereby limiting involuntary urine flow.

2. The method of claim 1 further comprising removing said urinary incontinence device from said vagina.

3. The method of claim 1 further comprising housing said urinary incontinence device in an applicator to facilitate insertion into a woman's vagina.

4. The method of claim 3 further comprising allowing said resilient member to expand to a non-compressed state when removed from said applicator and inserted into a woman's vagina.

5. The method of claim 1 further comprising allowing said resilient member to expand up to about 25% from its compressed state.

6. The method of claim 1 further comprising allowing said resilient member to expand up to about 50% from its compressed state.

7. The method of claim 6 further comprising allowing said resilient member to expand up to about 100% from its compressed state.

8. The method of claim 1 further comprising constructing said non-absorbent urinary incontinence device from an inert, biocompatible material that does not attract or hold normal body secretions.

9. The method of claim 1 further comprising constructing said non-absorbent urinary incontinence device into an elongated member having a length of at least about 2 inches.

10. A method for alleviating female urinary incontinence comprising the steps of:

a) providing a non-absorbent urinary incontinence device having an initial cross-sectional area and an insertion end and a trailing end, said urinary incontinence device containing a non-absorbent material made of fibers and a compressed resilient member which is at least partially located approximate to said insertion end and which is capable of increasing said cross-sectional area of said urinary incontinence device when expanded;

b) inserting said urinary incontinence device into a woman's vagina with said insertion end entering first, said vagina having a vaginal canal with an inner periphery made up of right and left lateral walls, an anterior wall and a posterior wall, and said urinary incontinence device contacting at least two of said walls;

c) positioning said urinary incontinence device in a middle third of the length of said vaginal canal with said insertion end aligned adjacent to a woman's urethral sphincter muscle which is a part of a woman's urethral tube, said urinary incontinence device cooperating with a woman's symphysis pubis to sandwich said urethral tube therebetween;

d) allowing said resilient member to expand within said woman's vagina such that at least a portion of said urinary incontinence device increases in cross-sectional area and contacts all four interior walls of said vaginal canal and provides a supportive backdrop for said urethral tube; and e) permitting said urethral tube to be compressed upon itself between said urinary incontinence device and said symphysis pubis thereby limiting involuntary urine flow.

11. The method of claim 10 further comprising removing said urinary incontinence device from said vagina.

12. The method of claim 10 further comprising constructing said non-absorbent urinary incontinence device into an elongated member having a length of from between about 2 inches to about 4 inches.

13. The method of claim 10 wherein said vaginal canal has a length of from between about four inches to about six inches and said urinary incontinence device is positioned in the middle two inches.

14. The method of claim 10 wherein said urethra has a length of about 1.5 inches and said urinary incontinence device provides a supportive backdrop for at least half of this distance.

15. A method for alleviating female urinary incontinence comprising the steps of:

a) providing a non-absorbent urinary incontinence device having an initial cross-sectional area and an insertion end and a trailing end, said urinary incontinence device containing a non-absorbent material made of fibers and a compressed resilient member which is capable of increasing said cross-sectional area of said urinary incontinence device when expanded;

b) inserting said urinary incontinence device into a woman's vagina with said insertion end entering first, said vagina having a vaginal canal with an inner periphery made up of right and left lateral walls, an anterior wall and a posterior wall, and said urinary incontinence device contacting at least two of said walls;

c) positioning said urinary incontinence device in a middle third of the length of said vaginal canal with said insertion end aligned adjacent to a woman's urethral sphincter muscle which is a part of a woman's urethral tube, said urinary incontinence device cooperating with a woman's symphysis pubis to sandwich said urethral tube therebetween;

d) allowing said resilient member to expand within said woman's vagina and contacts all four interior walls of said vaginal canal thereby spanning the cross-sectional area of said vagina and providing support for a woman's fundus vesicae; and e) permitting said urethral tube to be compressed upon itself between said urinary incontinence device and said symphysis pubis thereby limiting involuntary urine flow.

16. The method of claim 15 further comprising removing said urinary incontinence device from said vagina.

17. The method of claim 15 further comprising housing said urinary incontinence device in an applicator to facilitate insertion into a woman's vagina.

18. The method of claim 17 further comprising allowing said resilient member to expand to a non-compressed state when removed from said applicator and inserted into a woman's vagina.

19. The method of claim 15 further comprising constructing said nonabsorbent urinary incontinence device into an elongated member having a length of at least about 2 inches.

20. The method of claim 15 wherein said urethra has a length of about 1.5 inches and said urinary incontinence device provides a supportive backdrop for at least half of this distance.

21. A method for alleviating female urinary incontinence comprising the steps of:

a) providing a non-absorbent urinary incontinence device having an initial cross-sectional area and an insertion end and a trailing end, said urinary incontinence device containing a non-absorbent material made of fibers and a compressed resilient member which is capable of increasing said cross-sectional area of said urinary incontinence device when expanded;

b) inserting said urinary incontinence device into a woman's vagina with said insertion end entering first, said vagina having a vaginal canal with an inner periphery made up of right and left lateral walls, an anterior wall and a posterior wall, and said urinary incontinence device contacting at least two of said walls;

c) positioning said urinary incontinence device in a middle third of the length of said vaginal canal with said insertion end aligned adjacent to a woman's urethral sphincter muscle which is a part of a woman's urethral tube, and said urinary incontinence device cooperating with a woman's symphysis pubis to sandwich said urethral tube therebetween;

d) allowing said resilient member to expand within said vaginal canal such that at least a portion of said urinary incontinence device increases in cross-sectional area and contacts all four interior walls of said vaginal canal and occupies the entire void area of said vagina, said urinary incontinence device providing a supportive backdrop for said urethral tube; and e) permitting said urethral tube to be compressed upon itself between said urinary incontinence device and said symphysis pubis thereby limiting involuntary urine flow.

* * * * *